United States Patent [19]

Scher

[11] 4,053,627
[45] Oct. 11, 1977

[54] CONTROLLED RELEASE SYSTEM FOR JUVENILE HORMONES IN AQUEOUS ENVIRONMENT

[75] Inventor: Herbert B. Scher, Moraga, Calif.

[73] Assignee: Stauffer Chemical Company, Westport, Conn.

[21] Appl. No.: 612,129

[22] Filed: Sept. 10, 1975

[51] Int. Cl.$^2$ .............................................. A01N 9/28
[52] U.S. Cl. ..................................... 424/278; 424/19; 424/128; 424/343; 424/361; 424/DIG. 12
[58] Field of Search ................. 424/34, 278, 343, 361, 424/128, 19, DIG. 12

[56] References Cited
U.S. PATENT DOCUMENTS 2,441,729   5/1948   Steiner ................................ 424/361
3,907,783   9/1975   Pallos et al. ......................... 424/278

OTHER PUBLICATIONS

Chemical Abstracts, vol. 72 (1970), p. 54029w.
Merck Index, 8th Ed. (1968), p. 792.

Primary Examiner—V. D. Turner
Attorney, Agent, or Firm—Harry A. Pacini

[57] ABSTRACT

Controlled release of juvenile hormones into aqueous environment is accomplished with aliginate gel discs containing the juvenile hormone; said gel discs comprising a solubilizing agent, a water soluble algin, a salt which yields cations which gelatinize alginates, a biocide and a juvenile hormone, such as 4-ethylphenyl geranyl ether epoxide.

3 Claims, No Drawings

CONTROLLED RELEASE SYSTEM FOR JUVENILE HORMONES IN AQUEOUS ENVIRONMENT

This invention relates to a system for the controlled release of juvenile hormones in an aqueous environment. More particularly, this invention relates to alginate gel discs containing juvenile hormones, said discs being capable of controlled release of incorporated juvenile hormones. The said products have improved capabilities for durable and effective controlled release of incorporated juvenile hormones.

It is an object of this invention to provide new and improved alginate gel compositions and method for producing said composition containing a juvenile hormone.

It is a further object of this invention to provide alginate gel discs suitable for controlled release of juvenile hormones in an aqueous environment..

This invention is suitable for use in producing a wide variety of improved controlled release alginate gel discs. Said alginate gel discs may also be made for industrial, as well as agricultural purposes, employing such materials as deodorants, insecticides, biocides and the like.

The instant invention is particularly suitable for producing alginate gel discs containing a juvenile hormone by incorporating in the compositions of the invention various levels of ingredients in order to control the degradation of the gel discs in an aqueous environment.

It has been found that a further problem exists related to the chemical degradation of unprotected juvenile hormone when applied to an aqueous environment. Whereas, it is desirable to maintain the effectiveness of the juvenile hormone over a period of time, the methods of protecting the juvenile hormone from rapid release and chemical degradation in a water system present the problem to which this invention is directed.

In using the technique of juvenile hormones as insect control systems, there is considerable dependance on when the materials are applied and also on the dosage used. In order for the juvenile hormones or compounds with similar action to be effective, their application generally must be carefully timed to coincide with the insects' immature stage. Because of the action of the juvenile hormones which interrupts the normal development of the insect intermediate between the larvae and pupal stages, this timing is critical. Generally, insect growth regulators such as the juvenile hormones, show special promise in controlling mosquitoes, horn flies, bean beetles, potato beetles and other insects that are most damaging in the adult stage.

It is well known that water soluble alginates react with soluble calcium salts to form insoluble calcium alginate gels. The patent literature discloses the product of such gels with various algin compositions. Thus, for example, U.S. Pat. No. 2,441,729 discloses the manufacture of such gels from water soluble algin, calcium salts, a weak acid such as acetic or citric, and a gel retarding salt such as sodium hexametaphosate. Further algin gel compositions are disclosed in U.S. Pat. No. 2,918,375, issued Dec. 22, 1959. This patent discloses gel compositions similar to the compositions disclosed in U.S. Pat. No. 2,441,729 and it is directed to an improvement over the said patent in which adipic or fumaric acid is employed as the acid ingredient.

In general, the known method for producing an algin gel as disclosed in the literature as exemplified by the aforementioned U.S. Patents, is to employ a water soluble alginate as a source of algin and a calcium salt as a source of the calcium required to gelatinize the algin by converting it into an insoluble calcium alginate gel. On the addition of the free acid to the mixture of sodium alginate and a calcium salt, the calcium salt is slowly ionized to yield calcium ions, these free ions then reacting with the soluble alginate to form insoluble calcium alginate. The calcium ions are removed from solution in this manner, more are liberated and thus gelation proceeds through the gradual ionization of the calcium salt and the rate of gelation will be governed by the rate at which this ionization takes place. This in turn is governed by the inherent ionizability of the calcium salt, on the strength and concentration of the acid used, on the temperature obtained, and on the nature and amount of gel retarding salt such as the above-mentioned sodium hexametaphosphate. Further, it has been found that the controlled release properties of the alginate gel discs of the present invention can be varied by varying the molecular weight of the alginate, the alginate concentration, the type of polyvalent cation cross-linking agent (such as calcium, zinc, aluminum, copper or silver), the concentration of the cation, the ratio of mannuronic and gluronic acids in the alginate, and the concentration of non-cross-linking cations such as sodium.

In accordance with the present invention, it has been found that certain alginate gel disc compositions are suitable for controlled release of juvenile hormones in aqueous environments. This is particularly useful for controlling mosquitoes in flood water, ponds, and the like.

For convenience in describing the ingredients of the improved release system employing alginate gel discs, further information is set forth below as to the method and ingredients employed.

A water soluble algin. This may be the alginate of ammonium, magnesium, potassium, sodium or other alkali metal, or the alginate of an organic base such as mono-, di- or tri- ethanolamine, aniline, and the like. These soluble algins may be prepared by well known methods such as disclosed in the following U.S. Pat. Nos. 1,814,981, 2,036,922, 2,036,934 and 2,128,551.

Viscosity of the algin is not critical, although the higher viscosity algins form stronger gels than those of lower viscosity. If the compositions are usually prepared in the dry form, the algin is comminuted. The favorable grain size depends on the usage of the composition. An especially preferred water soluble alginate for the purpose of the present invention is a commercial grade of fibrous sodium alginate sold by Kelco Company, San Diego, California, known as Kelgin XL.

A salt which yields cations, which gelatinizes alginates, preferably of calcium, which either is insoluble or very slightly soluble in water, or which in aqueous solution is only slightly ionized, or both, and which on the addition of a solubilizing agent yields cations which gelatinizes alginates is used in this system. This might otherwise be defined as an algin-gelatinizing salt having a low solubility product. Further, the salt is an aqueous medium must not yield any material number of cations, which gelatinize the alginic component, until the solubilizing agent reacts with the salt.

Examples are tricalcium phosphate, dicalcium phosphate, calcium carbonate, calcium sulfate, calcium tartrate. Salts of the other alkali-earth metals (with the exception of magnesium which forms water soluble alginates) may be substituted for the calcium salts. This includes many of the heavy metals which may be substituted for calcium salts. Therefore, the polyvalent cation cross-linking agent may include calcium, zinc, aluminum, copper and silver.

It will be understood that in the above remarks, the reference to the calcium salts is intended to be illustrative only. The same principles apply in the use of corresponding salts of the other alkali earth metals and of the heavy metals.

In addition to the ingredients mentioned in the previous paragraph, a solubilizing agent is also employed. This component may be one of the alkali metal salts of such acids as citric and the various phosphoric acids. These solubilize the calcium salt and control gel formation by competing for the calcium ion. In general, these inhibitors are salts of weak acids. Particularly suitable materials for this purpose are sodium tripolyphosphate and sodium hexametaphosphate.

Other ingredients may be added to the alginate gel discs in order to improve their quality. For example, the dition of a biocide, such as sodium pentachlorophenate, will improve the performance of the discs by protecting the discs from attack by microorganisms. Similarly, various solvents may be used in order to facilitate the solubilization of the alginates. For example, in the present invention, ethylene glycol is used as a solvent to facilitate solubilization of the alginate.

Additionally, if desired, surface active agents, wetting agents, and dispersion promoters can be incorporated into the formulation to promote wetting and better dispersion of the juvenile hormone through the gel medium. The amount of juvenile hormone is a predetermined effective quantity shown to produce the desired insect growth regulating result upon application of the alginate gel discs into the aqueous environment. The following example is given to illustrate the present invention, but it is not to be construed as limiting the invention.

EXAMPLE

Alginate gel discs were produced for testing to determine the controlled degradation of the disc and controlled release of the incorporated insect juvenile hormone in water. The effects of juvenile hormone loading, calcium ion level and sodium tripolyphosphate level on the gellation period, gel quality and rate of gel degradation in water were determined. Alginated gel discs having the following composition were prepared.

A method for preparing certain geranyl phenyl ethers and their epoxides useful in controlling insects as juvenile insect hormones is described in U.S. Pat. No. 3,907,783, issued Sept. 23, 1975. The action of these type of compounds is described therein as insecticides which act as a disrupting influence upon the normal development of insects. Such compounds impede the metamorphosis of the normal pupation of pest insects and result in the formation of members of the treated species which are non-viable or sterile. This leads ultimately to the destruction of the pest population.

TABLE

| | |
|---|---|
| Sodium tripolyphosphate (STP) | 0.5 g. |
| Dowcide G** | 0.2 g. |
| Water | 84.7 g. |
| R-20458 4E (67% R-20458 tech)* | 5.0 g. |
| Kelgin XL (sodium alginate) | 5.0 g. |
| Ethylene glycol | 8.0 g. |
| Calcium sulfate | 1.6 g. |
| TOTAL | 105.0 g. |

*4-ethylphenyl geranyl ether epoxide
**sodium pentachlorophenate

The gel prepared using the following procedure:
1. Dissolve 0.5 g. sodium tripolyphosphate and 0.2 g. Dowcide G in 79.4 g. water. Add 0.5 g. R-20458 4E and mix;
2. slurry 0.5 g. Kelgin XL in 8.0 g. ethylene glycol. Add slurry to the mixture from (1) and mix for 15 minutes. The viscosity increases as the alginate dissolves. The oil phase (R-20458 4E) is emulsified to 1-2 $\mu$ particles (microscopic observation);
3. slurry 1.6 g. anhydrous calcium sulfate in 5.3 g. water and add to the alginate emulsion. Mix for 5 minutes and then pour very viscous mixture into aluminum weighing dishes. A firm gel forms in 2 to 4 hours. R-20458-solvent particles (1-2 $\mu$) are encapsulated in the gel.

From varying the quantities of juvenile hormone, R-20458 4E, calcium sulfate and sodium tripolyphosphate, various gelation periods, properties of gel and rate of degradation of gel in water were obtainable. It was found that the maximum possible R-20458 4E loading was approximately 10% by weight. The rate of degradation of the gel discs in water can be varied from days to years by varying the amount of calcium sulfate. The calcium ions cross-link the alginate molecules by complexing with carboxyl groups. The calcium ions must be made available gradually. The sodium tripolyphosphate, the solubilizing agent, aids in the gradual dissolution of the calcium sulfate. It was also found that sodium tripolyphosphate levels greater than 2.0 g., or approximately 2% by weight, resulted in no gelation.

When the alginate gel discs of the present invention were bioassayed against the juvenile hormone in a technical form in oxidation pond water with mosquito as the test species, the following results were obtained.

TABLE

| MOSQUITO RESIDUAL BIOASSAY IN OXIDATION POND WATER | | | | | |
|---|---|---|---|---|---|
| | Juvenile | $LD_{50}$ (ppm) at Indicated Day | | | |
| Formulation Type | Hormone % | 2 | 6 | 9 | 12 |
| Alginate gel disc | 3.2 | | <.01 | <.01 | <.01 |
| R-20458 tech | | <.01 | .2 | >.5 | >.5 |

The alginate gel disc containing R-20458 tested in the above mosquito residual bioassay showed that the alginate gel protected the juvenile hormone ($LD_{50}$ <0.01 ppm to 12 days), whereas the unprotected R-20458 tech lost its effectiveness between 2 and 6 days ($LD_{50}$ 2 days <0.01 ppm; $LD_{50}$ 6 days 0.2 ppm).

It will be appreciated that the description herein is illustrative of the present invention with various changes and modifications possible without departing from the scope and spirit of the invention herein described. These various changes and modifications will be apparent to those skilled in the art to which it pertains. It is accordingly intended that the present invention shall only be limited by the scope of the claims.

What is claimed is:

1. A method for the controlled release and protecting of an insect juvenile hormone from chemical degradation when said hormone is applied to an aqueous environment employing gel discs, said discs comprising a water soluble algin, a calcium salt which yields cations which gelatinize alginates, a solubilizing agent to control gel formation, a biocidally effective amount of a biocide to protect said discs from attack by microorganisms and an insect juvenile hormone.

2. The method of claim 1 in which the solubilizing agent is sodium tripolyphosphate, the water soluble algin is sodium alginate, the salt which yields cations is calcium sulfate, the biocide is sodium pentachlorophenate, and the insect juvenile hormone is 4-ethylphenyl geranyl ether epoxide.

3. The method of claim 2 in the form of a gel comprising the insect juvenile hormone in an amount up to and including about 10% by weight and solubilizing agent is up to and including 2% by weight.

* * * * *